United States Patent [19]

Satula et al.

[11] Patent Number: 5,021,645
[45] Date of Patent: Jun. 4, 1991

[54] PHOTOELECTRIC COLOR SENSOR FOR ARTICLE SORTING

[75] Inventors: Keith O. Satula, Waukesha; Russell P. Schuchmann, Milwaukee; Eugene F. Duncan, Wauwatosa, all of Wis.

[73] Assignee: Eaton Corporation, Cleveland, Ohio

[21] Appl. No.: 378,570

[22] Filed: Jul. 11, 1989

[51] Int. Cl.$^5$ ............................................. G01N 9/04
[52] U.S. Cl. ................................. 250/223 R; 250/226; 209/580
[58] Field of Search .................... 250/226, 223 R; 209/576, 577, 580

[56] References Cited

U.S. PATENT DOCUMENTS

| | | | |
|---|---|---|---|
| 3,526,777 | 9/1970 | Robinson | 250/237 |
| 3,910,701 | 10/1975 | Henderson et al. | 250/226 |
| 3,914,601 | 10/1975 | Hoover et al. | 250/226 |
| 4,003,660 | 1/1977 | Christie Jr. et al. | 356/178 |
| 4,093,991 | 6/1978 | Christie Jr. et al. | 364/525 |
| 4,529,308 | 7/1985 | Rife | 356/323 |
| 4,558,786 | 12/1985 | Lane | 250/226 |
| 4,699,273 | 10/1987 | Suggi-Liverani et al. | 250/223 R |
| 4,711,580 | 12/1987 | Venable | 356/406 |
| 4,716,285 | 12/1987 | Konishi | 250/226 |
| 4,784,275 | 11/1988 | Fridge | 209/580 |
| 4,812,904 | 3/1989 | Maring et al. | 358/107 |
| 4,820,915 | 4/1989 | Hamakawa et al. | 250/211 J |
| 4,823,185 | 4/1989 | Miyamoto et al. | 250/226 |
| 4,917,500 | 4/1990 | Lugos | 356/406 |

OTHER PUBLICATIONS

AEG Aktiengesellschaft Product Brochure, "Photo-Electronics A Convincing Manufacturing Programme", Dated 02/87.

PRC Krochmann GMBH Brochure, "Colorimeter 420, Data Sheet May 1987".
LMT Lichtmesstechnik GMBH Berlin Brochure, "LMT Products 1987".
Handbook of Optics, Optical Society of America, Walter G. Driscoll, ed., McGraw Hill, 1978, pp. 9-1 Thru 9-40.
BVD Bilddatenverarbeiting, Prof. Dr. Robert Massen, Brochure "Colour & Shape".
ESD: The Electronic System Design Magazine, Jan. 1988, p. 38 et seq. Imaging and Graphics Article.
Siemens, Optoelectronic Data Book, 1987/88, Preliminary Data Sheets LDB5410, pp. 5-13-5-14 and "Blue Light Emitting Silicon-Carbide Diodes-Materials, Technology, Characteristics" by Dr. Class Wayrick, pp. 11-75-11-77.

Primary Examiner—David C. Nelms
Assistant Examiner—Khaled Shami
Attorney, Agent, or Firm—L. G. Vande Zande

[57] ABSTRACT

A device for photoelectrically sensing the color of a target object includes two more light sources having different characteristic ranges of chromaticity and at least one photosensitive element which receives light from the light sources after it has reflected off of the target object. A logic circuit serves to serially energize the light sources and receive resultant sample signals from the photosensitive elements. The logic circuit then generates a resultant signal as a function of the various sample signals and compares the resultant signal with a predetermined reference standard. If the difference therebetween exceeds a tolerance limit, the control circuit will output a reject signal.

18 Claims, 4 Drawing Sheets

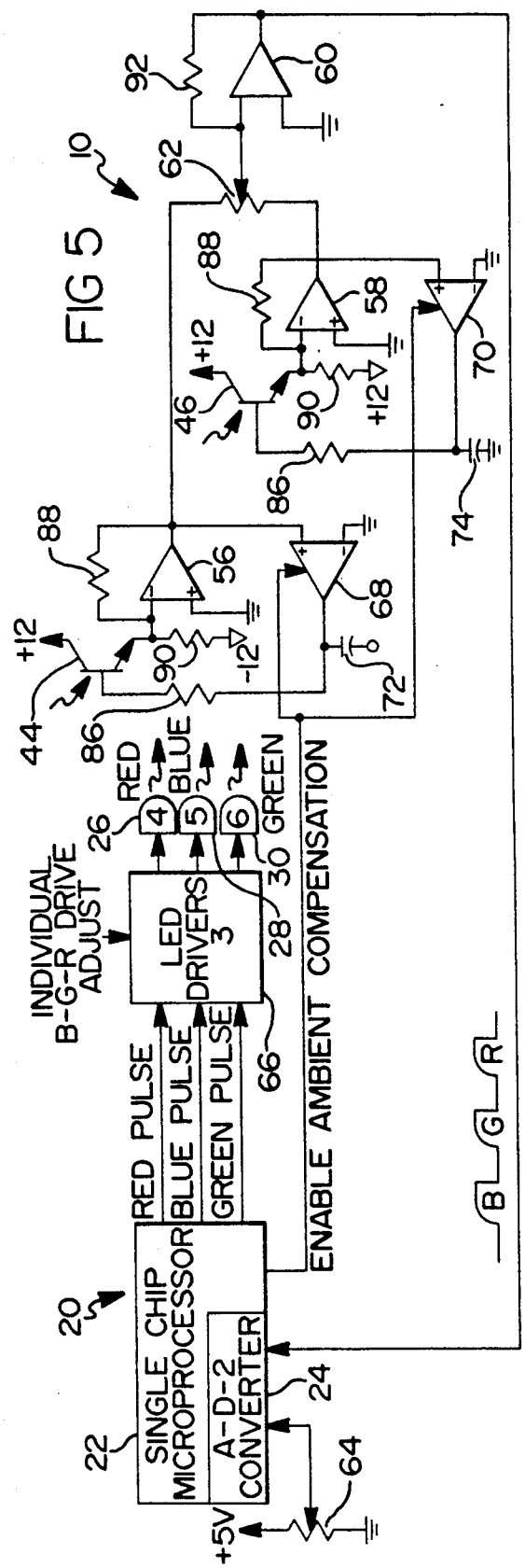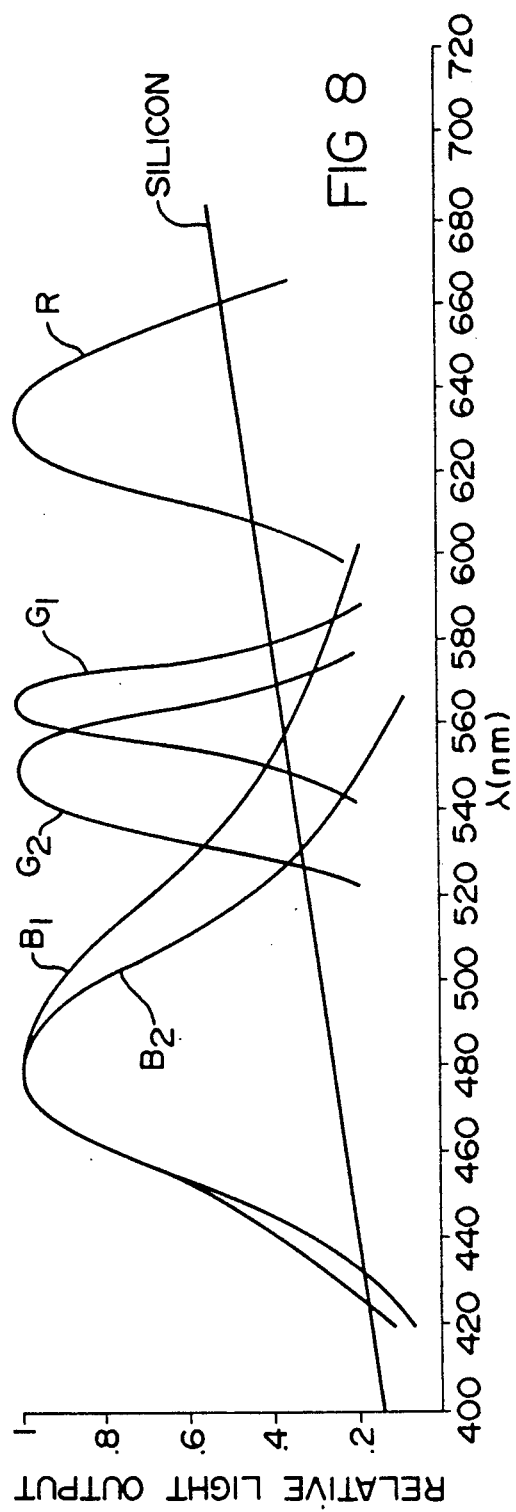

PHOTOELECTRIC COLOR SENSOR FOR ARTICLE SORTING

TECHNICAL FIELD

The present invention relates to an apparatus suitable for machine vision applications. Specifically, the present invention relates to sensing systems which can receive and process color information for inspection purposes. More particularly still, the present invention relates to an apparatus for determining the correctness of a target object's color.

BACKGROUND OF THE INVENTION

The ability to quantify and reliably identify color has proven to be illusive. The perception of color has historically proved to be highly subjective. The matter is further complicated by the existence of several ways to specify color. For example, manufacturers of color monitors, video cameras and computer graphics often define color as a combination of the primary colors—red, green and blue (RGB). These additive primaries can be mixed in any combination to produce millions of colors in the visible spectrum. Another traditional color specification method, popular in the publishing industry for mixing inks, is based on combining the subtractive primaries—cyan, yellow, magenta and black (CYMK). Television broadcasting represents color in yet another method; RGB signals are encoded in luminescence (Y) and chrominance (I&Q) signals to facilitate broadcasting.

Recent advancements in optics and microelectronics is tending to expand color imaging into many fields including manufacturing process control, robotics and the like. Today, color is a very important factor in maintaining the overall quality of pharmaceuticals, food products and the like. Because the physical appearance of a product is frequently equated to a perceived if not actual standard of quality, it is incumbent upon a manufacturer to maintain consistency from unit to unit as well as to maintain adherence to specified product standards. By incorporating a color discerning sensor on a line as part of the manufacturing/production process, much more product can be monitored than heretofore was available with recognized off-line measurement techniques, ensuring that only acceptable product is produced. Subjective judgments as to appearance are no longer required whereby continuous product consistency can be achieved.

Although the foregoing concepts are widely recognized and accepted in principle, currently available color sensor technology has a number of deficiencies, limiting the applications thereof in many areas. Present sensors are typically, extremely expensive, bulky and are sensitive to ambient light changes and heat. As a result, sensors are typically employed off-line. Sensors which are used on-line frequently have their sensing heads and processing logic separated by bundles of fiber optic cables wherein the head is positioned to contact or be closely spaced from the target object and the processing portion of the device is physically remote to protect it from the manufacturing process. In the food industry, the problem is reversed in that the goods being produced are extremely susceptible to outside sources of heat and real estate on the production line tends to be extremely limited.

A further limitation of many prior art color sensing devices resides in their extremely short lifetime, requiring frequent shutting down of the production process to replace the sensor's light source or other failed components. Furthermore, because widely accepted prior art approaches at processing color information tend to be laborious, system response time suffers whereby such devices are not suitable for many applications requiring high speed processing.

Although color sensors are frequently employed with powerful data processors, they frequently are incapable of learning; that is, to compare color component information with prior process history to reprogram the system to adjust tolerances, anticipate changing ambient conditions and the like. To the contrary, prior art devices typically compare a simple measured signal with a derived fixed standard. Lastly, such devices also typically have a very limited sensitivity and, although able to differentiate one pure color from another, are incapable of discriminating between slightly varying hues of the same color.

BRIEF DESCRIPTION OF THE INVENTION

The present invention provides a new and improved apparatus for rapidly determining the color of a target object as well as differentiating changes in hue of the target color extremely rapidly and cost effectively. The apparatus is packaged for convenient on-line application adjacent the product flow. Furthermore, the present inventive apparatus is adaptive, able to learn and remember the color of prior sensed target objects and to adapt to changing conditions.

The apparatus of the present invention comprises at least two sources of light disposed in a fixed array and focused upon a sensing region. Each source is operable to emit light having a limited characteristic range of chromaticity which differs from that of the other range or ranges. Photosensitive means are positionally fixed with respect to the array of light sources to receive light from each source which has been reflected off of a target object within the sensing region and to output a signal in response thereto. Logic means are connected in circuit with the light sources and photosensitive means which is operative to sequentially energize each light source and to receive resultant sample signals from the photosensitive means in response to the light source energization. The logic means is further operative to generate a resultant signal as a function of the sample signals, to compare the resultant signal with a predetermined reference standard and to generate a condition output signal when the difference between the resultant signal and reference standard exceeds a tolerance limit. This arrangement has the advantage of providing a compact assemblage of inexpensive components with simple yet adaptive local processing in a configuration well suited for on-line manufacturing process control. Furthermore, this arrangement provides for serial processing of multiple signals of differing frequency ranges which are subsequently combined for enhanced logical processing speed and reliability.

According to another aspect of the invention the light sources comprise red, green and blue LEDs disposed in a common plane with their mutual focal point within the target sensing region and the photosensitive means comprise at least one phototransistor disposed in a plane common with the central blue LED and the focal point normal to the LED plane of arrangement. This arrangement ensures that the line of travel from each LED to the target and back to the phototransistor is the same.

According to another aspect of the invention, the photosensitive means includes two phototransistors which straddle the center (blue) LED. This arrangement permits differential processing to offset errors induced by variances in target position between successive targets.

According to still another aspect of the invention, the logic means includes first and second amplifiers each of which are operative to generate a respective element signal in response to the light source energization. A third amplifier is provided to output the aforesaid sample signals as a function of both the first and second element signal. This arrangement provides the differential processing discussed hereinabove. Further, the logic means comprises a circuit operative to drain electrical current from the base junction of the phototransistors whenever all of the light emitting diodes are deenergized to offset the effect of ambient induced photocurrent in the phototransistors. This arrangement has the advantage of providing for ambient light compensation without affecting the speed or responsiveness of the color sensor.

These and other features and advantages of the present invention will become apparent upon reading the following specification, which, along with the patent drawings, describes and discloses a preferred embodiment of the invention in detail.

A detailed description of the embodiment of the invention makes reference to the accompanying drawings.

BRIEF DESCRIPTION OF THE DRAWINGS

FIG. 5, is a schematic diagram of the preferred embodiment of the present inventive photoelectric color sensor;

FIG. 8, is a graphical correlation of the wave length/relative output of the various light sources employed in the present invention.

DETAILED DESCRIPTION OF THE PREFERRED EMBODIMENT OF THE INVENTION

Figure 1:
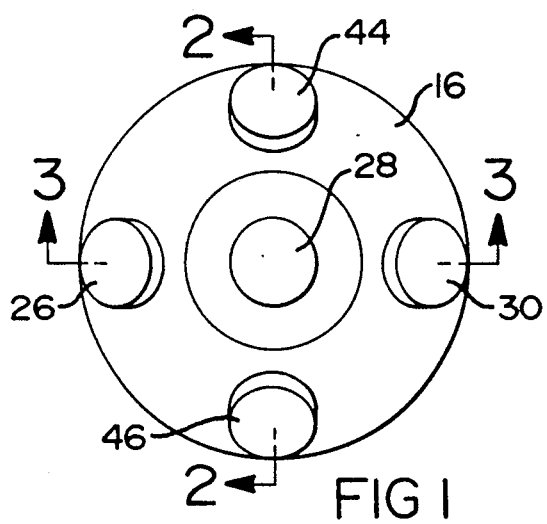
FIG. 1, is a top plan view of a sensor head employed in the preferred embodiment of the present invention.

Referring the drawing figures, a photoelectric color sensor 10 is illustrated which, in its intended application, is to compare the color of both ends of a pharmaceutical capsule 12 to the desired color for a particular product. Capsules 12 move past the sensor 10 on a conveyor line indicated generally by arrow 14 as they are inspected. As will be described in detail hereinbelow, sensor 10 performs a go, no-go comparison of sensed color to stored color data. Two sets of color data corresponding to the opposite ends of the capsule 12 are stored so that the color of both capsule ends can be inspected. The sensor 10 provides a reject signal if either end of the capsule 12 does not match one of the stored colors. Logic is provided to accept the capsule with either color first in the sequence. When the first color is found to be one of the acceptable colors, the second color must correspond to the remaining reference color. Sensor 10 is provided with a learn mode activated manually by a learn/run switch wherein color data from a reference capsule presented to the sensor in the learn mode is stored. In application, a succession of capsules 12 is presented to sensor 10 for color identification at a fixed vertical distance from the sensor head 16. In practice, sensor 10 can accommodate a lateral displacement of capsule 12 by an amount equal to plus or minus 10% of the capsule width as indicated in phantom in FIG. 2.

When implemented with componentry of the values specified hereinbelow, sensor 10 can sample and identify the color of both ends of a capsule within 3 ms. For allocating the time during the identification cycle, it is assumed that the 3 ms interval between capsules 12 occurs over a spatial distance of two capsule lengths, i.e. only half of the space is actually occupied by capsules. Sensor head 16 includes a shield (not illustrated) to minimize the intrusion of ambient light. However, as shall be described in detail hereinbelow, sensor 10 can accommodate residual ambient light from normal room lighting that may enter the target area or sensing region, shown generally at 18, beneath the edges of the light shield. It is contemplated that sensor 10 shall receive a marker signal from a host system to indicate the presence of a capsule 12. Sensor 10 makes provision for a second marker signal to provide a reference mark for the middle of capsule 12. Sensor 10 also makes provision for generating an internal time reference for the middle of the capsule based upon uniform line speed and timed from the first marker. Sensor 10 provides a solid state N-type reject output usable with a 10-30 VDC N-type input. The output of sensor 10 may be short-circuit protected. Sensor 10 makes quantitative measurements of red, blue, and green light reflection from the target capsule 12 when illuminated with suitable light sources. The color identification algorithm shall compare this color data using suitable tolerances, to stored color data obtained during the learn mode. Sensor 10 includes a logic circuit 20 employing an eight-bit single chip microprocessor 22 with internal A-D converters 24, and accepts the aforesaid marker signals, generates the timing cycle for internal sensor functions, provides set-up modes, captures and processes color data and provides a reject output signal. It is contemplated that suitable function and output indicators will be provided as well as an appropriate source of power. For the sake of simplicity, a number of above described incidental or peripheral circuit elements are not described in detail herein, it being understood that such functions are well understood by those of ordinary skill in the art and that suitable componentry is commercially available.

Figure 2:
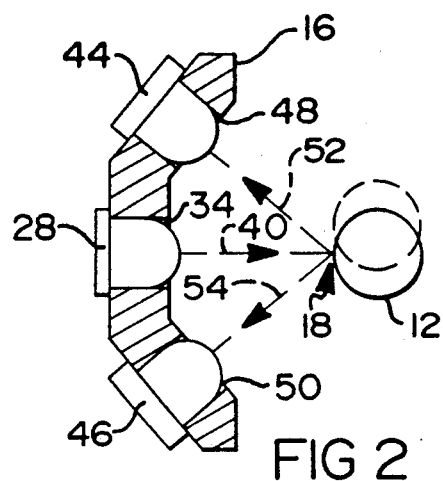
FIG. 2, is a cross sectional side view of the sensor head taken on lines 2—2 of FIG. 1.
Figure 3:
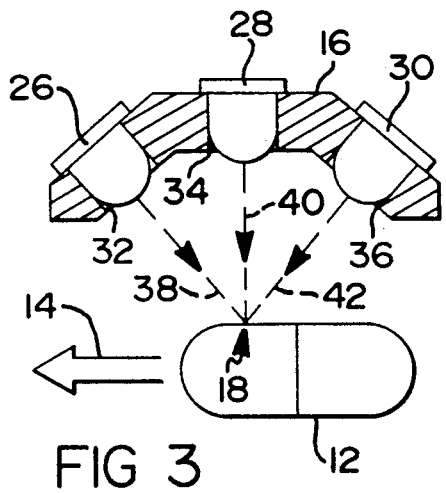
FIG. 3, is a cross sectional bottom view of the sensor head taken on lines 3—3 of FIG. 1.

Referring to FIGS. 1-3, sensor head 16 is generally dish-shaped and formed of an opaque material. Red, blue and green light emitting diodes (hereafter LEDs) are received within through bores 32, 34 and 36, respectively, within sensor head 16. When energized, LEDs 26, 28 and 30 will emit light along a principle axis indicated by arrows 38, 40 and 42, mutually converging upon a focal point upon the surface of capsule 12 within sensing region 18. Likewise, two phototransistors 44 and 46 are received within through bores 48 and 50, respectively. Phototransistors 44 and 46 are each positioned whereby its light receiving axis 52 and 54, respectively, are inwardly converging upon the focal point of LEDs 26, 28 and 30. The axes of symmetry of LEDs 26, 28 and 30, axes 38, 40 and 42 as well as their focal point fall within a fixed plane generally corresponding with the section cut line 3—3 of FIG. 1. Likewise, LED 28, phototransistors 44 and 46 as well as their respective axes 40, 52 and 50 fall on a common plane which is normal to the plane of LEDs 26, 28 and 30. Accordingly, phototransistors 44 and 46 are positioned to be mutually equidistant from each of the LEDs 26, 28 and 30 along the line of light incidence and reflection off of capsule 12. The blue LED 28 is located in a favored position in the center of the head to compensate for lower light output capability than the red and green LEDs 26 and 30.

Figure 4:
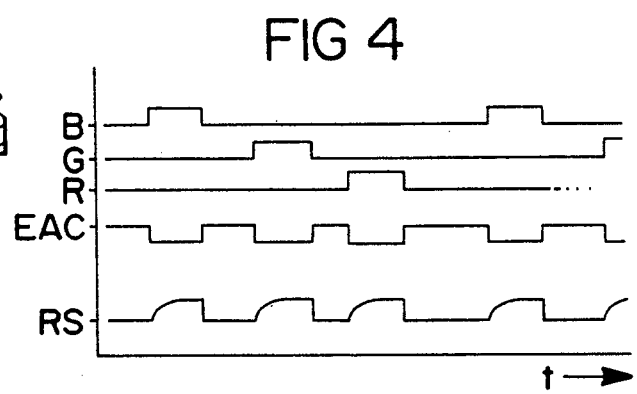
FIG. 4, is a signal timing chart correlating various relationships within the present invention.

Referring to FIG. 4, LEDs 26, 28 and 30 are driven sequentially by logic circuit 20 to illuminate capsule 12 with blue, green and red light as illustrated. The reflected light from each color is detected by phototransistors 44 and 46 (see FIG. 5), amplified by operational amplifiers 56 and 58, respectively, and summed in operational amplifier 60. A potentiometer 62 has its fixed resistance portion across the outputs of op amps 56 and 58 and the wiper connected to the input of op amp 60 to balance sensitivity variations between phototransistors 44 and 46 Op amp 60 outputs resultant sample signals to A-D converter 24 within microprocessor 22. Microprocessor 22 generates timing pulses for the red, blue and green LEDs 26, 28 and 30, respectively, and in synchronism with each pulse samples the output of amplifier 60 and converts it to a digital value. These digital values for each color are stored in memory and may be processed with any of several algorithms to determine the color of the target being viewed. One such known algorithm or conversion relationships are known as Munsell equations which describes an exact color by way of a vector on a circle with its origin at the center of the circle. Alternatively, the red, green and blue values may be compared to a stored set of colors obtained by viewing a reference color during a "learn" mode at set-up. This is functionally described in FIG. 7. For this mode, a second potentiometer 64 is connected to a second A-D converter 24 channel of microprocessor 22 which is proportional to the tolerance to be used when comparing the red, green and blue signals to a set of stored reference values. As discussed hereinabove, more than one set of color reference values can be stored for use in, for example, sequentially checking the color of both ends of a pharmaceutical capsule 12.

Figure 6:
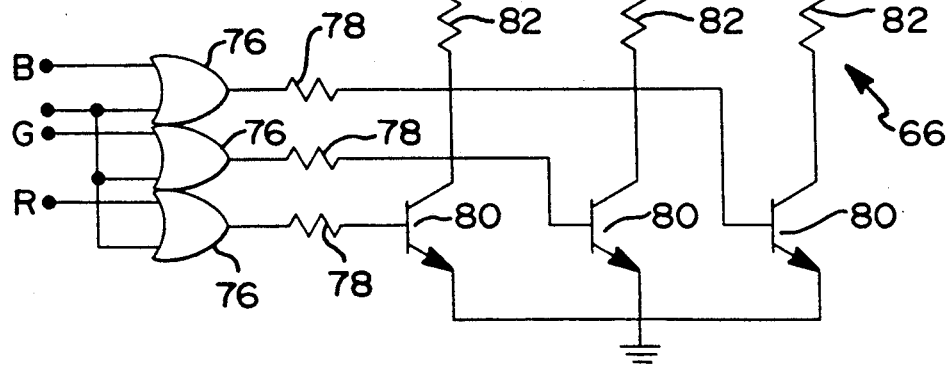
FIG. 6, is a schematic diagram of the LED driver portion of the schematic of FIG. 5.

Red, green and blue pulses from microprocessor 22 drive LED drivers 66 as shown in FIG. 6 which can be adjusted to individually control the red, green and blue LED currents through use of a digitally controlled gain circuit established by the microprocessor 22 and programmable feedback resistance in the final gain stage amplifier circuit 92 (FIG. 5). These are adjusted to provide equal red, green and blue pulse amplitudes out of amplifier 60 when a white target is viewed. This adjustment compensates both for variation in light output versus current among the LEDs and for variations in phototransistor 44 and 46 over the spectral range. An additional drive stage may be added to the blue LED 28 to provide ±12 volt bias for enhanced output.

Sensor 10 is made substantially insensitive to steady state ambient light through the provision of ambient compensating loops consisting of operational transconductance amplifiers 68 and 70, and capacitors 72 and 74. Operational transconductance amplifiers 68 and 70 function as amplifiers only when enabled by the ambient compensation enable (EAC) signals shown in FIG. 4, which are true whenever none of the red, blue and green LEDs 26, 28 and 30, respectively, are energized. Otherwise, the output of amplifiers 68 and 70 are an open circuit which does not provide a discharge path for the voltage stored in capacitors 72 and 74. When amplifiers 68 and 70 are energized, a voltage is stored on capacitors 72 and 74 which withdraws current from the base of the respective phototransistor 44 and 46 to compensate for ambient induced photocurrent in phototransistors 44 and 46. Capacitors 72 and 74 are large enough to retain this voltage during the signal measurement intervals when amplifiers 68 and 70 are not energized. The lowermost signal trace in FIG. 4 represent the resultant sample (RS) signals received by microprocessor 22 from amplifier 60.

The balance of the componentry illustrated in FIGS. 5 and 6 are listed hereinbelow, it being understood that they represent only one of any number of variants upon the represent invention inventive concept.

| REF. NO. | TYPE | VALUE/TYPE |
| --- | --- | --- |
| 22 | Microprocessor | BGHCC11 |
| 26 | LED | HLMP3750 |
| 28 | LED | LDB5410 (Siemens) |
| 30 | LED | HLMP3950 |
| 44,46 | Phototransistors | OP805 |
| 56,58,60 | Op Amps | 34080 |
| 68,70 | Op Amps | CA3080 |
| 76 | OR Gate | CD4081 |
| 78 | Resistor | 1 Kohm |
| 80 | Transistor | 2N3904 |
| 82 | Resistor | 220 ohm |
| 84 | Potentiometer | 2 Kohm |
| 86 | Resistor | 100 Kohm |
| 88 | Resistor | 50 Kohm |
| 90 | Resistor | 100 Kohm |
| 92 | Resistor | 20 Kohm |

Referring to FIG. 8, the relative light output amplitude versus frequency characteristic derived for two blue, two green and one red commercially available LEDs is presented to illustrate that each diode in the red, green and blue categories have their own characteristic limited range of chromaticity which substantially differs from the others and that collectively they substantially encompass the entire visible light spectrum.

Figure 9:
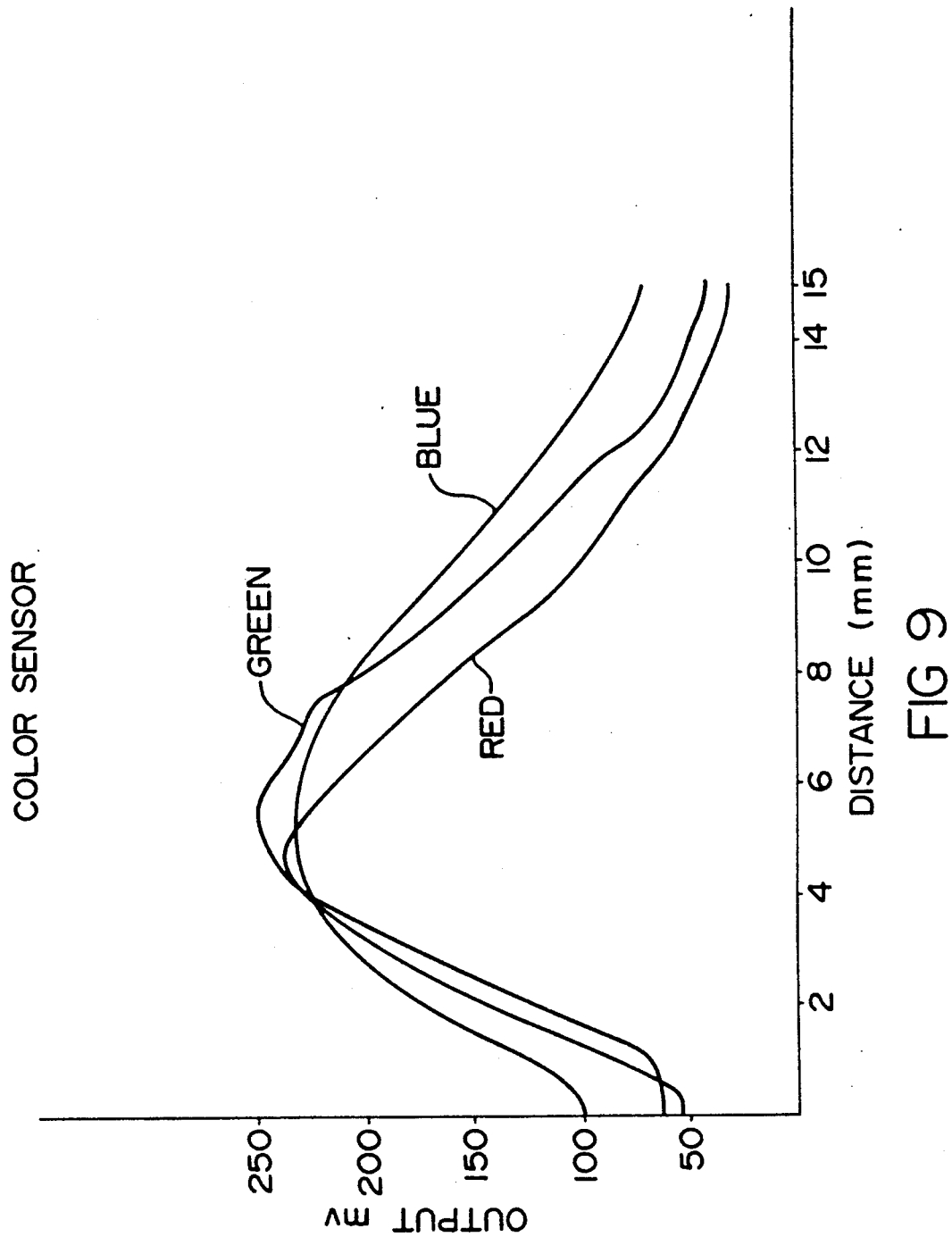
FIG. 9, is a graphical presentation of experimentally derived color sensor output versus distance (from target) data.

Referring to FIG. 9, the experimentally derived relationship of output versus distance of the target capsule 12 from the focal point is illustrated to highlight the color to color registration of sensitivities within the present invention.

Figure 7:
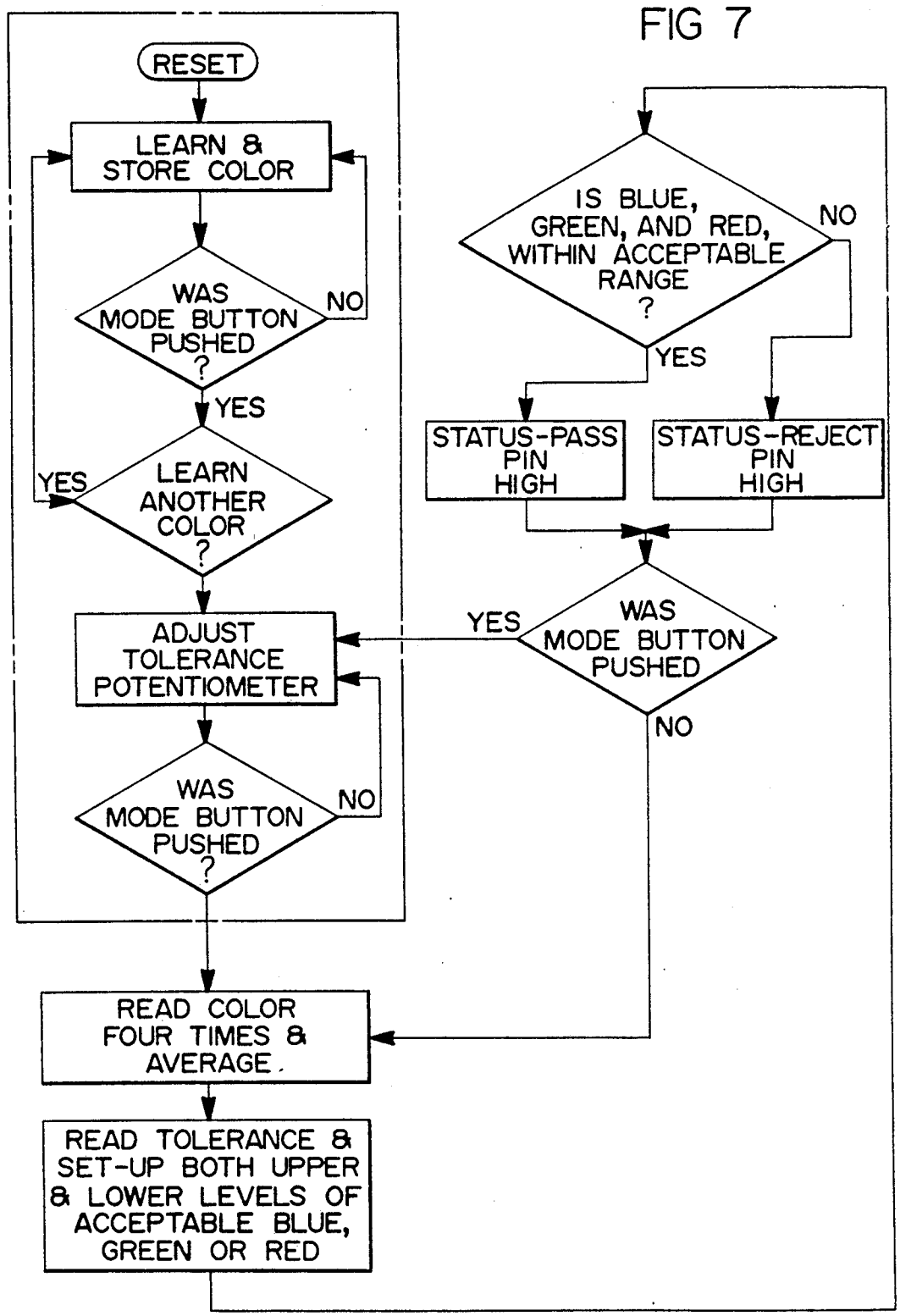
FIG. 7, is a simplified flow chart of software implemented in the microprocessor of the present invention.

Referring to FIG. 7, the basic logic program within microprocessor 22 is illustrated. The single-chip microprocessor 22 adds intelligence and versatility to the color sensing system 10 in a way that would be difficult to achieve by discrete means such as through programmable logic devices. The microprocessor chip 22 performs three general tasks in the operation of the color sensor 10. (1) it maintains control of the emitting and receiving photodiodes 26, 28, 30, 44 and 46, (2) it provides input analysis and response to the collected sensor data, (3) it manages local and remote communication interfaces. These functions are primarily originated by software driven inputs and outputs from the microprocessor chip 22. Each of these functions are expounded upon below.

The first sensor control task (1) is provided by software algorithms which switch the red, green and blue LEDs 26, 30 and 28 on and off in a proper order in conjunction with the inversion of the autozero signal. Routines are also available for a programmable gain control on the receiving input amplifier, thus allowing for self calibration, in order to adjust to target applications of varying reflective gains. The routine attempts to achieve a linear but maximal gain for all three hues without driving the receiving amplifier into saturation for any individual hue. Circuitry and software is in place to provide an interrupt mechanism which permits triggering of the sensor readings based upon target presence or relative position in the sensor field of view. Initiation of this triggering mechanism can be accomplished through remote programming or by on-board dip switches. There are several pushbuttons on the sensor that are interpreted by the microprocessor. The mode button is a multipurpose control switch for progressing the sensor operation from a learn-color mode to the normal run mode of operation. In particular, the first push of the mode button out of reset will learn the color in the sensor view, another push will cause it to learn the second color if the device has been previously configured for more than one color. After learning colors the next push puts it in the tolerance setting mode, and the next would put it in the normal run mode. If the mode button is pushed in the run mode, the device again returns to the tolerance set mode.

The second task (2) of the microcomputer chip 22 is for data analysis. After measuring the analog input and converting it to digital information, one of several paths can be taken to analyze the data, based on user preconfigured settings. The input readings may or may not be averaged, the choice being determined by how much response speed versus noisy signal suppression that is desired. Averaging slows the response time of the device but increases repeatability in the color determination. The readings may or may not be normalized, that is where each individual hue or LED light reflection reading is expressed as a ratio of the total of all three hue readings. The chief consequence of dealing with absolute rather than normalized voltage values for hue is that it renders the analysis more susceptible to variations in intensity of the reflected light due to sensor-to-target distance variation; this is not a problem when normalized. However, if the intensity of the reflected light can be held relatively constant, absolute readings will distinguish different tones of the same color hue, while normalizing masks the distinction. One-color or multi-color sensing can be selected by dip switch or remote terminal programming as well. In the current design, the output of the color analysis is made up of two go/no-go control lines which provide a go/no-go signal. One line fires high for a passing color, the other for a failure of the color match to the stored standard. Each line has a corresponding LED indicator for demonstration purposes. When there is a match to any stored color, the go-signal pin fires. Plug-in external sensors may serve as marker inputs to distinguish which color is being tested at a given time (mentioned above as part of the triggering mechanism.

The third task (3) incorporates the elements of the user interface. Simple interface elements are provided such as the reset button, which restarts the device and sets it in the learn color mode. The second button is the mode button, which as described above, progresses the device operation sequentially through the available modes. LED indicators under the control of the microprocessor, distinguish the state of the device operation. These indicators are the learn versus run mode, color good versus bad, learn color versus tolerance set mode, first color or second color learn, and power-on LEDs. User defined set-up configurations can be entered in two ways. The operating configuration can be set by either switching a bank of dip switches located on the sensor (local) or by serially communicating to the sensor from a (remote) personal computer or dumb ASCII terminal. Serial communication software is available in the microcomputer chip coding. Serial communication can be initiated during the run mode which will return the operating state to the learn mode.

It is to be understood that the invention has been described with reference to a specific embodiment to provide the features and advantages previously described and that such specific embodiments are susceptible of modification, such as will be apparent to those skilled in the art. For example, the preferred embodiment of the invention represents an application specific design for a particular shape target object as well as a specific set of colors and hues. Furthermore feedback resistor 92 can be replaced by a potentiometer or a programmable resistor to selectively adjust the gain of amplifier 60. Also any number of color standards can be learned and stored and any number of readings can be averaged. It is contemplated that the above recited component values and arrangements could be varied without departing from the spirit of this invention. Accordingly, the foregoing is not to be construed in a limiting sense.

```
******************************************************
*           CONTROL PROGRAM FOR COLOR SENSOR         *
******************************************************
* Assembly Source Code
* Microprocessor:  Motorola 68HC811E2
*
*
*
* Sensor Product Development, Dept. H-57
* EATON CORPORATION
* (C) 1988
*
```

```
1000              REGBAS    EQU    $1000
0000              PORTA     EQU    $00
0004              PORTB     EQU    $04
1003              PORTC     EQU    $1003
000E              TCNT      EQU    $0E
0016              TOC1      EQU    $16
0020              TCTL1     EQU    $20
0022              TMSK1     EQU    $22
0023              TFLG1     EQU    $23
0024              TMSK2     EQU    $24
0025              TFLG2     EQU    $25
0030              ADCTL     EQU    $30
0031              ADR1      EQU    $31
0032              ADR2      EQU    $32
0033              ADR3      EQU    $33
0034              ADR4      EQU    $34
0039              OPTION    EQU    $39
003A              COPRST    EQU    $3A
0000                        ORG    $0000
0000              COLORFLG  RMB    1
0001              LEDOUT    RMB    1
0002              IRQPOLL   RMB    1
0003              BLUE      RMB    2
0005              GREEN     RMB    2
0007              RED       RMB    2
0009              TOLERSET  RMB    2
000B              RGBSUM    RMB    2
000D              BLUE1     RMB    2
000F              GREEN1    RMB    2
0011              RED1      RMB    2
0013              RGBSUM1   RMB    2
0015              BLUE2     RMB    2
0017              GREEN2    RMB    2
0019              RED2      RMB    2
001B              RGBSUM2   RMB    2
001D              BTOL1U    RMB    2
001F              BTOL1L    RMB    2
0021              GTOL1U    RMB    2
0023              GTOL1L    RMB    2
0025              RTOL1U    RMB    2
0027              RTOL1L    RMB    2
0029              BTOL2U    RMB    2
002B              BTOL2L    RMB    2
002D              GTOL2U    RMB    2
002F              GTOL2L    RMB    2
0031              RTOL2U    RMB    2
0033              RTOL2L    RMB    2
0035              N1BLUE    RMB    2
0037              N1GREEN   RMB    2
0039              N1RED     RMB    2
003B              N2BLUE    RMB    2
003D              N2GREEN   RMB    2
003F              N2RED     RMB    2
0041              IRQTRIG   RMB    1
0042              DISTINCT  RMB    1
0043              IC1TRIG   RMB    1
```

```
0044            IC2TRIG     RMB     1
0045            COUNTER     RMB     1
0046            ABSFLAG     RMB     1
0047            AVEFLAG     RMB     1
0048            ONECOLOR    RMB     1
0049            AVECNTR     RMB     1
004A            BLUEX       RMB     2
004C            GREENX      RMB     2
004E            REDX        RMB     2
0050            RGBSUMX     RMB     2
FFF2                        ORG     $FFF2
FFF2 FD 0C                  FDB     IRQHND
FFFA                        ORG     $FFFA
FFFA FD 21                  FDB     COPOUT
FFFC                        ORG     $FFFC
FFFC FD 2A                  FDB     CPMHND
FFFE                        ORG     $FFFE
FFFE F8 00                  FDB     BEGIN
FFF8                        ORG     $FFF8
FFF8 FD 88                  FDB     ILLHND
FFEC                        ORG     $FFEC
FFEC FD 88                  FDB     IC2HND
FFEE                        ORG     $FFEE
FFEE FD 8E                  FDB     IC1HND
FFF6                        ORG     $FFF6
FFF6 FD 94                  FDB     SWIHND
FFF4                        ORG     $FFF4
FFF4 FD 91                  FDB     XIQHND
F800                        ORG     $F800
F800 CE 10 00   BEGIN:      LDX     #REGBAS
        *                   BCLR    OPTION,X %00000011
F803 A6 39                  LDAA    OPTION,X
F805 8A 20                  ORAA    #%00100000
F807 A7 39                  STAA    OPTION,X
F809 8E 00 FF               LDS     #$00FF
F80C 0E                     CLI
F80D CC 00 00               LDD     #$0000
F810 97 00                  STAA    COLORFLG
F812 97 01                  STAA    LEDOUT
F814 97 02                  STAA    IRQPOLL
F816 97 41                  STAA    IRQTRIG
F818 97 42                  STAA    DISTINCT
F81A 97 43                  STAA    IC1TRIG
F81C 97 44                  STAA    IC2TRIG
F81E 97 45                  STAA    COUNTER

F820 DD 03                  STD     BLUE
F822 DD 05                  STD     GREEN
F824 DD 07                  STD     RED
F826 DD 09                  STD     TOLERSET
F828 DD 0B                  STD     RGBSUM
F82A DD 0D                  STD     BLUE1
F82C DD 0F                  STD     GREEN1
F82E DD 11                  STD     RED1
F830 DD 13                  STD     RGBSUM1
F832 DD 15                  STD     BLUE2
```

```
F834 DD 17                      STD    GREEN2
F836 DD 19                      STD    RED2
F838 DD 1B                      STD    RGBSUM2
F83A DD 2B                      STD    BTOL2L
F83C DD 2F                      STD    GTOL2L
F83E DD 33                      STD    RTOL2L
F840 DD 1F                      STD    BTOL1L
F842 DD 23                      STD    GTOL1L
F844 DD 27                      STD    RTOL1L
F846 CC FF FF                   LDD    #$FFFF
F849 DD 1D                      STD    BTOL1U
F84B DD 21                      STD    GTOL1U
F84D DD 25                      STD    RTOL1U
F84F DD 29                      STD    BTOL2U
F851 DD 2D                      STD    GTOL2U
F853 DD 31                      STD    RTOL2U
F855 DD 4A                      STD    BLUEX
F857 DD 4C                      STD    GREENX
F859 DD 4E                      STD    REDX
F85B DD 50                      STD    RGBSUMX
F85D 86 FF                      LDAA   #$FF
F85F 97 48                      STAA   ONECOLOR
F861 97 46                      STAA   ABSFLAG
F863 97 47                      STAA   AVEFLAG
F865 86 04                      LDAA   #$04
F867 97 49                      STAA   AVECNTR
F869 CE 10 00                   LDX    #REGBAS
F86C 86 C8                      LDAA   #%11001000
F86E A7 04                      STAA   PORTB,X
F870 84 F7                      ANDA   #%11110111
F872 A7 04                      STAA   PORTB,X
F874 86 FF                      LDAA   #$FF
F876 A7 23                      STAA   TFLG1,X
F878 86 80                      LDAA   #%10000000
F87A A7 39                      STAA   OPTION,X
F87C EC 0E                      LDD    TCNT,X
F87E C3 00 C8                   ADDD   #200
F881 ED 16                      STD    TOC1,X
F883 1F 23 80 FC    LOOP1:      BRCLR  TFLG1,X $80 LOOP1
F887 0C                         CLC
F888 12 48 FF 02                BRSET  ONECOLOR $FF GOLRN2
F88C 20 03                      BRA    LEARN1
F88E 7E F9 30       GOLRN2:     JMP    LEARN2
F891 0F             LEARN1:     SEI
F892 86 04                      LDAA   #$04
F894 97 49                      STAA   AVECNTR
F896 CC 00 00                   LDD    #$0000
F899 DD 0D                      STD    BLUE1
F89B DD 0F                      STD    GREEN1
F89D DD 11                      STD    RED1
F89F DD 13                      STD    RGBSUM1
F8A1 CE 10 00                   LDX    #REGBAS
F8A4 86 60                      LDAA   #%01100000
F8A6 97 01                      STAA   LEDOUT
F8A8 86 E0                      LDAA   #%11100000
F8AA A7 04                      STAA   PORTB,X
```

```
F8AC 8D FA B6        RPTLRH1:    JSR    READVALS
F8AF 13 47 FF 37                 BRCLR  AVEFLAG $FF NOAVE1
F8B3 DC 0D                       LDD    BLUE1
F8B5 D3 03                       ADDD   BLUE
F8B7 DD 0D                       STD    BLUE1
F8B9 DC 0F                       LDD    GREEN1
F8BB D3 05                       ADDD   GREEN
F8BD DD 0F                       STD    GREEN1
F8BF DC 11                       LDD    RED1
F8C1 D3 07                       ADDD   RED
F8C3 DD 11                       STD    RED1
F8C5 DC 13                       LDD    RGBSUM1
F8C7 D3 0B                       ADDD   RGBSUM
F8C9 DD 13                       STD    RGBSUM1
F8CB 7A 00 49                    DEC    AVECNTR
F8CE 26 DC                       BNE    RPTLRH1
F8D0 DC 0D                       LDD    BLUE1
F8D2 04                          LSRD
F8D3 04                          LSRD
F8D4 DD 0D                       STD    BLUE1
F8D6 DC 0F                       LDD    GREEN1
F8D8 04                          LSRD
F8D9 04                          LSRD
F8DA DD 0F                       STD    GREEN1
F8DC DC 11                       LDD    RED1
F8DE 04                          LSRD
F8DF 04                          LSRD
F8E0 DD 11                       STD    RED1
F8E2 DC 13                       LDD    RGBSUM1
F8E4 04                          LSRD
F8E5 04                          LSRD
F8E6 DD 13                       STD    RGBSUM1
F8E8 20 10                       BRA    AV1DONE
F8EA DC 03           NOAVE1:     LDD    BLUE
F8EC DD 0D                       STD    BLUE1
F8EE DC 05                       LDD    GREEN
F8F0 DD 0F                       STD    GREEN1
F8F2 DC 07                       LDD    RED
F8F4 DD 11                       STD    RED1
F8F6 DC 0B                       LDD    RGBSUM
F8F8 DD 13                       STD    RGBSUM1
F8FA 0E              AV1DONE:    CLI
F8FB 12 46 FF 17                 BRSET  ABSFLAG $FF ABS1
F8FF DC 0D                       LDD    BLUE1
F901 DE 13                       LDX    RGBSUM1
F903 03                          FDIV
F904 DF 35                       STX    N1BLUE
F906 DC 0F                       LDD    GREEN1
F908 DE 13                       LDX    RGBSUM1
F90A 03                          FDIV
F90B DF 37                       STX    N1GREEN
F90D DC 11                       LDD    RED1
F90F DE 13                       LDX    RGBSUM1
F911 03                          FDIV
F912 DF 39                       STX    N1RED
F914 20 0C                       BRA    IRQCHK1
```

```
F916 DC 0D          ABS1:      LDD   BLUE1
F918 DD 35                     STD   N1BLUE
F91A DC 0F                     LDD   GREEN1
F91C DD 37                     STD   N1GREEN
F91E DC 11                     LDD   RED1
F920 DD 39                     STD   N1RED
F922 12 41 FF 03    IRQCHK1:   BRSET IRQTRIG $FF PRLEARN2
F926 7E F8 91                  JMP   LEARN1
F929 0F             PRLEARN2:  SEI
F92A 7F 00 41                  CLR   IRQTRIG
F92D 7E F9 30                  JMP   LEARN2
F930 0F             LEARN2:    SEI
F931 86 04                     LDAA  #$04
F933 97 49                     STAA  AVECNTR
F935 CC 00 00                  LDD   #$0000
F938 DD 15                     STD   BLUE2
F93A DD 17                     STD   GREEN2
F93C DD 19                     STD   RED2
F93E DD 1B                     STD   RGBSUM2
F940 CE 10 00                  LDX   #REGBAS
F943 86 50                     LDAA  #%01010000
F945 97 01                     STAA  LEDOUT
F947 86 D0                     LDAA  #%11010000
F949 A7 04                     STAA  PORTB,X
F94B BD FA B6       RPTLRN2:   JSR   READVALS
F94E 13 47 FF 37               BRCLR AVEFLAG $FF NOAVE2
F952 DC 15                     LDD   BLUE2
F954 D3 03                     ADDD  BLUE
F956 DD 15                     STD   BLUE2
F958 DC 17                     LDD   GREEN2
F95A D3 05                     ADDD  GREEN
F95C DD 17                     STD   GREEN2
F95E DC 19                     LDD   RED2
F960 D3 07                     ADDD  RED
F962 DD 19                     STD   RED2
F964 DC 1B                     LDD   RGBSUM2
F966 D3 0B                     ADDD  RGBSUM
F968 DD 1B                     STD   RGBSUM2
F96A 7A 00 49                  DEC   AVECNTR
F96D 26 DC                     BNE   RPTLRN2
F96F DC 15                     LDD   BLUE2
F971 04                        LSRD
F972 04                        LSRD
F973 DD 15                     STD   BLUE2
F975 DC 17                     LDD   GREEN2
F977 04                        LSRD
F978 04                        LSRD
F979 DD 17                     STD   GREEN2
F97B DC 19                     LDD   RED2
F97D 04                        LSRD
F97E 04                        LSRD
F97F DD 19                     STD   RED2
F981 DC 1B                     LDD   RGBSUM2
F983 04                        LSRD
F984 04                        LSRD
F985 DD 1B                     STD   RGBSUM2
```

```
F987 20 10                   BRA    AV2DONE
F989 DC 03       NOAVE2:     LDD    BLUE
F98B DD 15                   STD    BLUE2
F98D DC 05                   LDD    GREEN
F98F DD 17                   STD    GREEN2
F991 DC 07                   LDD    RED
F993 DD 19                   STD    RED2
F995 DC 0B                   LDD    RGBSUM
F997 DD 1B                   STD    RGBSUM2
F999 0E          AV2DONE:    CLI
F99A 12 46 FF 17             BRSET  ABSFLAG $FF ABS2
F99E DC 15                   LDD    BLUE2
F9A0 DE 1B                   LDX    RGBSUM2
F9A2 03                      FDIV
F9A3 DF 3B                   STX    N2BLUE
F9A5 DC 17                   LDD    GREEN2
F9A7 DE 1B                   LDX    RGBSUM2
F9A9 03                      FDIV
F9AA DF 3D                   STX    N2GREEN
F9AC DC 19                   LDD    RED2
F9AE DE 1B                   LDX    RGBSUM2
F9B0 03                      FDIV
F9B1 DF 3F                   STX    N2RED
F9B3 20 0C                   BRA    IRQCHK2
F9B5 DC 15       ABS2:       LDD    BLUE2
F9B7 DD 3B                   STD    N2BLUE
F9B9 DC 17                   LDD    GREEN2
F9BB DD 3D                   STD    N2GREEN
F9BD DC 19                   LDD    RED2
F9BF DD 3F                   STD    N2RED
F9C1 12 41 FF 03 IRQCHK2:    BRSET  IRQTRIG $FF PRTOLSET
F9C5 7E F9 30                JMP    LEARN:
F9C8 0F          PRTOLSET:   SEI
F9C9 7F 00 41                CLR    IRQTRIG
F9CC 7E F9 CF                JMP    TOLSET
F9CF 0F          TOLSET:     SEI
F9D0 86 40                   LDAA   #%01000000
F9D2 97 01                   STAA   LEDOUT
F9D4 86 C0                   LDAA   #%11000000
F9D6 A7 04                   STAA   PORTB,X
F9D8 BD FA B6                JSR    READVALS
F9DB 13 46 FF 06             BRCLR  ABSFLAG $FF NOADJTOL
F9DF DC 09                   LDD    TOLERSET
F9E1 16                      TAB
F9E2 4F                      CLRA
F9E3 DD 09                   STD    TOLERSET
F9E5 0E          NOADJTOL:   CLI
F9E6 DC 35                   LDD    N1BLUE
F9E8 D3 09                   ADDD   TOLERSET
F9EA DD 1D                   STD    BTOL1U
F9EC DC 35                   LDD    N1BLUE
F9EE 93 09                   SUBD   TOLERSET
F9F0 2A 03                   BPL    BTOL1
F9F2 CC 00 00                LDD    #$0000
F9F5 DD 1F       BTOL1:      STD    BTOL1L
F9F7 DC 37                   LDD    N1GREEN
F9F9 D3 09                   ADDD   TOLERSET
```

```
F9F8 DD 21                    STD    GTOL1U
F9FD DC 37                    LDD    N1GREEN
F9FF 93 09                    SUBD   TOLERSET
FA01 2A 03                    BPL    GTOL1
FA03 CC 00 00                 LDD    #$0000
FA06 DD 23         GTOL1:     STD    GTOL1L
FA08 DC 39                    LDD    N1RED
FA0A D3 09                    ADDD   TOLERSET
FA0C DD 25                    STD    RTOL1U
FA0E DC 39                    LDD    N1RED
FA10 93 09                    SUBD   TOLERSET
FA12 2A 03                    BPL    RTOL1
FA14 CC 00 00                 LDD    #$0000
FA17 DD 27         RTOL1:     STD    RTOL1L
FA19 DC 3B                    LDD    N2BLUE
FA1B D3 09                    ADDD   TOLERSET
FA1D DD 29                    STD    BTOL2U
FA1F DC 3B                    LDD    N2BLUE
FA21 93 09                    SUBD   TOLERSET
FA23 2A 03                    BPL    BTOL2
FA25 CC 00 00                 LDD    #$0000
FA28 DD 2B         BTOL2:     STD    BTOL2L
FA2A DC 3D                    LDD    N2GREEN
FA2C D3 09                    ADDD   TOLERSET
FA2E DD 2D                    STD    GTOL2U
FA30 DC 3D                    LDD    N2GREEN
FA32 93 09                    SUBD   TOLERSET
FA34 2A 03                    BPL    GTOL2
FA36 CC 00 00                 LDD    #$0000
FA39 DD 2F         GTOL2:     STD    GTOL2L
FA3B DC 3F                    LDD    N2RED
FA3D D3 09                    ADDD   TOLERSET
FA3F DD 31                    STD    RTOL2U
FA41 DC 3F                    LDD    N2RED
FA43 93 09                    SUBD   TOLERSET
FA45 2A 03                    BPL    RTOL2
FA47 CC 00 00                 LDD    #$0000
FA4A DD 33         RTOL2:     STD    RTOL2L
FA4C 13 48 FF 07              BRCLR  ONECOLOR $FF DISTCHK
FA50 86 1F                    LDAA   #$1F
FA52 97 42                    STAA   DISTINCT
FA54 7E FA 90                 JMP    SKIP3
FA57 DC 35         DISTCHK:   LDD    N1BLUE
FA59 93 3B                    SUBD   N2BLUE
FA5B 24 04                    BHS    NOTNEG1
FA5D DC 3B                    LDD    N2BLUE
FA5F 93 35                    SUBD   N1BLUE
FA61 04            NOTNEG1:   LSRD
FA62 1A 93 09                 CPD    TOLERSET
FA65 22 03                    BHI    SKIP1
FA67 14 42 9F                 BSET   DISTINCT %10011111
FA6A DC 37         SKIP1:     LDD    N1GREEN
FA6C 93 3D                    SUBD   N2GREEN
FA6E 24 04                    BHS    NOTNEG2
FA70 DC 3D                    LDD    N2GREEN
FA72 93 37                    SUBD   N1GREEN
```

```
FA74 04              NOTNEG2:   LSRD
FA75 1A 93 09                   CPD    TOLERSET
FA78 22 03                      BHI    SKIP2
FA7A 14 42 5F                   BSET   DISTINCT %01011111
FA7D DC 39           SKIP2:     LDD    N1RED
FA7F 93 3F                      SUBD   N2RED
FA81 24 04                      BHS    NOTNEG3
FA83 DC 3F                      LDD    N2RED
FA85 93 39                      SUBD   N1RED
FA87 04              NOTNEG3:   LSRD
FA88 1A 93 09                   CPD    TOLERSET
FA8B 22 03                      BHI    SKIP3
FA8D 14 42 3F                   BSET   DISTINCT %00111111
FA90 12 41 FF 06     SKIP3:     BRSET  IRQTRIG $FF FINISH
FA94 7F 00 42        TOLAGN:    CLR    DISTINCT
FA97 7E F9 CF                   JMP    TOLSET
FA9A 0F              FINISH:    SEI
FA9B 7F 00 41                   CLR    IRQTRIG
FA9E 96 42                      LDAA   DISTINCT
FAA0 81 FF                      CMPA   #$FF
FAA2 27 F0                      BEQ    TOLAGN
FAA4 CE 10 00                   LDX    #REGBAS
FAA7 86 90                      LDAA   #%10010000
FAA9 A7 04                      STAA   PORTB,X
FAAB 86 10                      LDAA   #%00010000
FAAD 97 01                      STAA   LEDOUT
FAAF 7E FB 2F                   JMP    RUNMODE
FAB2 01                         NOP
FAB3 01                         NOP
FAB4 01                         NOP
FAB5 01                         NOP
FAB6 CE 10 00        READVALS:  LDX    #REGBAS
FAB9 9A 01                      ORAA   LEDOUT
FABB A7 04                      STAA   PORTB,X
FABD 01                         NOP
FABE 01                         NOP
FABF 01                         NOP
FAC0 01                         NOP
FAC1 21 FE                      BRN    *
FAC3 C6 30                      LDAB   #%00110000
FAC5 E7 30                      STAB   ADCTL,X
FAC7 01                         NOP
FAC8 01                         NOP
FAC9 21 FE                      BRN    *
FACB 8A 80                      ORAA   #%10000000
FACD 84 E8                      ANDA   #%11111000
FACF A7 04                      STAA   PORTB,X
FAD1 01                         NOP
FAD2 01                         NOP
FAD3 01                         NOP
FAD4 01                         NOP
FAD5 01                         NOP
FAD6 01                         NOP
FAD7 01                         NOP
FAD8 01                         NOP
FAD9 21 FE                      BRN    *
FADB 01                         NOP
```

```
FADC 01                    NOP
FADD 86 02                 LDAA  #%00000010
FADF 9A 01                 ORAA  LEDOUT
FAE1 A7 04                 STAA  PORTB,X
FAE3 4F                    CLRA
FAE4 E6 31                 LDAB  ADR1,X
FAE6 DD 03                 STD   BLUE
FAE8 01                    NOP
FAE9 01                    NOP
FAEA 01                    NOP
FAEB 21 FE                 BRN   *
FAED 01                    NOP
FAEE 01                    NOP
FAEF 86 80                 LDAA  #%10000000
FAF1 9A 01                 ORAA  LEDOUT
FAF3 A7 04                 STAA  PORTB,X
FAF5 01                    NOP
FAF6 01                    NOP
FAF7 01                    NOP
FAF8 01                    NOP
FAF9 01                    NOP
FAFA 01                    NOP
FAFB 01                    NOP
FAFC 01                    NOP
FAFD 21 FE                 BRN   *
FAFF 01                    NOP
FB00 01                    NOP
FB01 86 01                 LDAA  #%00000001
FB03 9A 01                 ORAA  LEDOUT
FB05 A7 04                 STAA  PORTB,X
FB07 4F                    CLRA
FB08 E6 33                 LDAB  ADR3,X
FB0A DD 05                 STD   GREEN
FB0C D3 03                 ADDD  BLUE
FB0E DD 0B                 STD   RGBSUM
FB10 01                    NOP
FB11 01                    NOP
FB12 86 80                 LDAA  #%10000000
FB14 9A 01                 ORAA  LEDOUT
FB16 A7 04                 STAA  PORTB,X
FB18 01                    NOP
FB19 C6 FF                 LDAB  #$FF
FB1B A6 34                 LDAA  ADR4,X
FB1D DD 09                 STD   TOLERSET
FB1F 01                    NOP
FB20 01                    NOP
FB21 21 FE                 BRN   *
FB23 4F                    CLRA
FB24 E6 31                 LDAB  ADR1,X
FB26 DD 07                 STD   RED
FB28 A7 30                 STAA  ADCTL,X
FB2A D3 0B                 ADDD  RGBSUM
FB2C DD 0B                 STD   RGBSUM
FB2E 39                    RTS
FB2F 0F          RUNMODE:  SEI
FB30 86 C8                 LDAA  #200
FB32 97 49                 STAA  AVECNTR
```

```
FB34 CC 00 00              LDD   #$0000
FB37 DD 4A                 STD   BLUEX
FB39 DD 4C                 STD   GREENX
FB3B DD 4E                 STD   REDX
FB3D DD 50                 STD   RGBSUMX
FB3F 8D FA B6    RPTLRHX:  JSR   READVALS
FB42 13 47 FF 57           BRCLR AVEFLAG $FF NOAVEX
FB46 DC 4A                 LDD   BLUEX
FB48 D3 03                 ADDD  BLUE
FB4A DD 4A                 STD   BLUEX
FB4C DC 4C                 LDD   GREENX
FB4E D3 05                 ADDD  GREEN
FB50 DD 4C                 STD   GREENX
FB52 DC 4E                 LDD   REDX
FB54 D3 07                 ADDD  RED
FB56 DD 4E                 STD   REDX
FB58 DC 50                 LDD   RGBSUMX
FB5A D3 0B                 ADDD  RGBSUM
FB5C DD 50                 STD   RGBSUMX
FB5E 7A 00 49              DEC   AVECNTR
FB61 26 DC                 BNE   RPTLRHX
FB63 20 18                 BRA   TRUDIV
FB65 DC 4A                 LDD   BLUEX
FB67 04                    LSRD
FB68 04                    LSRD
FB69 DD 03                 STD   BLUE
FB6B DC 4C                 LDD   GREENX
FB6D 04                    LSRD
FB6E 04                    LSRD
FB6F DD 05                 STD   GREEN
FB71 DC 4E                 LDD   REDX
FB73 04                    LSRD
FB74 04                    LSRD
FB75 DD 07                 STD   RED
FB77 DC 50                 LDD   RGBSUMX
FB79 04                    LSRD
FB7A 04                    LSRD
FB7B DD 0B                 STD   RGBSUM
FB7D DE 4A       TRUDIV:   LDX   BLUEX
FB7F CC 00 C8              LDD   #200
FB82 02                    IDIV
FB83 DF 03                 STX   BLUE
FB85 DE 4C                 LDX   GREENX
FB87 CC 00 C8              LDD   #200
FB8A 02                    IDIV
FB8B DF 05                 STX   GREEN
FB8D DE 4E                 LDX   REDX
FB8F CC 00 C8              LDD   #200
FB92 02                    IDIV
FB93 DF 07                 STX   RED
FB95 DE 50                 LDX   RGBSUMX
FB97 CC 00 C8              LDD   #200
FB9A 02                    IDIV
FB9B DF 0B                 STX   RGBSUM
FB9D 0E          NOAVEX:   CLI
FB9E DC 03                 LDD   BLUE
FBA0 12 46 FF 04           BRSET ABSFLAG $FF ABSCHK1
```

```
FBA4 DE 0B              LDX  RGBSUM
FBA6 03                 FDIV
FBA7 8F                 XGDX
FBA8 1A 93 1F   ABSCHK1: CPD  BTOL1L
FBAB 25 0E              BLO  BH1
FBAD 1A 93 1D           CPD  BTOL1U
FBB0 22 17              BHI  BL1
FBB2 21 FE              BRN  *
FBB4 4F                 CLRA
FBB5 8A 80              ORAA #%10000000
FBB7 97 00              STAA COLORFLG
FBB9 20 16              BRA  BOVR1
FBBB 01         BH1:    NOP
FBBC 01                 NOP
FBBD 01                 NOP
FBBE 01                 NOP
FBBF 01                 NOP
FBC0 01                 NOP
FBC1 01                 NOP
FBC2 01                 NOP
FBC3 01                 NOP
FBC4 01                 NOP
FBC5 20 00              BRA  CONT1
FBC7 20 08      CONT1:  BRA  BOVR1
FBC9 01         BL1:    NOP
FBCA 01                 NOP
FBCB 01                 NOP
FBCC 01                 NOP
FBCD 01                 NOP
FBCE 01                 NOP
FBCF 01                 NOP
FBD0 01                 NOP
FBD1 DC 03      BOVR1:  LDD  BLUE
FBD3 1A 93 2B           CPD  BTOL2L
FBD6 25 0F              BLO  BH2
FBD8 1A 93 29           CPD  BTOL2U
FBDB 22 18              BHI  BL2
FBDD 21 FE              BRN  *
FBDF 96 00              LDAA COLORFLG
FBE1 8A 10              ORAA #%00010000
FBE3 97 00              STAA COLORFLG
FBE5 20 16              BRA  BOVR2
FBE7 01         BH2:    NOP
FBE8 01                 NOP
FBE9 01                 NOP
FBEA 01                 NOP
FBEB 01                 NOP
FBEC 01                 NOP
FBED 01                 NOP
FBEE 01                 NOP
FBEF 01                 NOP
FBF0 01                 NOP
FBF1 20 00              BRA  CONT2
FBF3 20 08      CONT2:  BRA  BOVR2
FBF5 01         BL2:    NOP
FBF6 01                 NOP
FBF7 01                 NOP
```

```
FBF8 01                         NOP
FBF9 01                         NOP
FBFA 01                         NOP
FBFB 01                         NOP
FBFC 01                         NOP
FBFD 12 46 FF 06    BOVR2:      BRSET ABSFLAG $FF ABSCHK2
FC01 DC 05                      LDD   GREEN
FC03 DE 08                      LDX   RGBSUM
FC05 03                         FDIV
FC06 8F                         XGDX
FC07 1A 93 23       ABSCHK2:    CPD   GTOL1L
FC0A 25 0F                      BLO   GH1
FC0C 1A 93 21                   CPD   GTOL1U
FC0F 22 18                      BHI   GL1
FC11 21 FE                      BRN   *
FC13 96 00                      LDAA  COLORFLG
FC15 8A 40                      ORAA  #%01000000
FC17 97 00                      STAA  COLORFLG
FC19 20 16                      BRA   GOVR1
FC1B 01             GH1:        NOP
FC1C 01                         NOP
FC1D 01                         NOP
FC1E 01                         NOP
FC1F 01                         NOP
FC20 01                         NOP
FC21 01                         NOP
FC22 01                         NOP
FC23 01                         NOP
FC24 01                         NOP
FC25 20 00                      BRA   GCONT1
FC27 20 08          GCONT1:     BRA   GOVR1
FC29 01             GL1:        NOP
FC2A 01                         NOP
FC2B 01                         NOP
FC2C 01                         NOP
FC2D 01                         NOP
FC2E 01                         NOP
FC2F 01                         NOP
FC30 01                         NOP
FC31 DC 05          GOVR1:      LDD   GREEN
FC33 1A 93 2F                   CPD   GTOL2L
FC36 25 0F                      BLO   GH2
FC38 1A 93 2D                   CPD   GTOL2U
FC3B 22 18                      BHI   GL2
FC3D 21 FE                      BRN   *
FC3F 96 00                      LDAA  COLORFLG
FC41 8A 08                      ORAA  #%00001000
FC43 97 00                      STAA  COLORFLG
FC45 20 16                      BRA   GOVR2
FC47 01             GH2:        NOP
FC48 01                         NOP
FC49 01                         NOP
FC4A 01                         NOP
FC4B 01                         NOP
FC4C 01                         NOP
FC4D 01                         NOP
```

```
FC4E 01                              NOP
FC4F 01                              NOP
FC50 01                              NOP
FC51 20 00                           BRA   GCONT2
FC53 20 08           GCONT2:         BRA   GOVR2
FC55 01              GL2:            NOP
FC56 01                              NOP
FC57 01                              NOP
FC58 01                              NOP
FC59 01                              NOP
FC5A 01                              NOP
FC5B 01                              NOP
FC5C 01                              NOP
FC5D 12 46 FF 06     GOVR2:          BRSET ABSFLAG $FF ABSCHK3
FC61 DC 07                           LDD   RED
FC63 DE 0B                           LDX   RGBSUM
FC65 03                              FDIV
FC66 8F                              XGDX
FC67 1A 93 27        ABSCHK3:        CPD   RTOL1L
FC6A 25 0F                           BLO   RH1
FC6C 1A 93 25                        CPD   RTOL1U
FC6F 22 18                           BHI   RL1
FC71 21 FE                           BRN   *
FC73 96 00                           LDAA  COLORFLG
FC75 8A 20                           ORAA  #%00100000
FC79 20 16                           BRA   ROVR1
FC7B 01              RH1:            NOP
FC7C 01                              NOP
FC7D 01                              NOP
FC7E 01                              NOP
FC7F 01                              NOP
FC80 01                              NOP
FC81 01                              NOP
FC82 01                              NOP
FC83 01                              NOP
FC84 01                              NOP
FC85 20 00                           BRA   RCONT1
FC87 20 08           RCONT1:         BRA   ROVR1
FC89 01              RL1:            NOP
FC8A 01                              NOP
FC8B 01                              NOP
FC8C 01                              NOP
FC8D 01                              NOP
FC8E 01                              NOP
FC8F 01                              NOP
FC90 01                              NOP
FC91 DC 07           ROVR1:          LDD   RED
FC93 1A 93 33                        CPD   RTOL2L
FC96 25 0F                           BLO   RH2
FC98 1A 93 31                        CPD   RTOL2U
FC9B 22 18                           BHI   RL2
FC9D 21 FE                           BRN   *
FC9F 96 00                           LDAA  COLORFLG
FCA1 8A 04                           ORAA  #%00000100
FCA3 97 00                           STAA  COLORFLG
FCA5 20 16                           BRA   ROVR2
FCA7 01              RH2:            NOP
```

```
FCA8 01                              NOP
FCA9 01                              NOP
FCAA 01                              NOP
FCAB 01                              NOP
FCAC 01                              NOP
FCAD 01                              NOP
FCAE 01                              NOP
FCAF 01                              NOP
FCB0 01                              NOP
FCB1 20 00                           BRA     RCONT2
FCB3 20 08         RCONT2:           BRA     ROVR2
FCB5 01            RL2:              NOP
FCB6 01                              NOP
FCB7 01                              NOP
FCB8 01                              NOP
FCB9 01                              NOP
FCBA 01                              NOP
FCBB 01                              NOP
FCBC 01                              NOP
FCBD 13 48 FF 06   ROVR2:            BRCLR   ONECOLOR $FF TWOCOL
FCC1 12 00 1C 17                     BRSET   COLORFLG %00011100 COLOR2
FCC5 20 08                           BRA     NOGOOD
FCC7 12 00 E0 0E   TWOCOL:           BRSET   COLORFLG %11100000 COLOR1
FCCB 12 00 1C 0D                     BRSET   COLORFLG %00011100 COLOR2
FCCF 86 10         NOGOOD:           LDAA    #%00010000
FCD1 97 01                           STAA    LEDOUT
FCD3 01                              NOP
FCD4 01                              NOP
FCD5 20 00                           BRA     ENP
FCD7 20 09         ENP:              BRA     SHOPULSE
FCD9 01            COLOR1:           NOP
FCDA 01                              NOP
FCDB 01                              NOP
FCDC 01            COLOR2:           NOP
FCDD 01                              NOP
FCDE 86 20                           LDAA    #%00100000
FCE0 97 01                           STAA    LEDOUT
FCE2 7F 00 00      SHOPULSE:         CLR     COLORFLG
FCE5 CE 10 00                        LDX     #REGBAS
FCE8 8A 80                           ORAA    #%10000000
FCEA A7 04                           STAA    PORTB,X
FCEC 01            CHKMODE:          NOP
FCED A6 00                           LDAA    PORTA,X
FCEF 84 01                           ANDA    #%00000001
FCF1 81 01                           CMPA    #%00000001
FCF3 27 06                           BEQ     AGAIN    ye
FCF5 12 43 FF 02                     BRSET   IC1TRIG $FF AGAIN
FCF9 20 F1                           BRA     CHKMODE
FCFB 7F 00 43      AGAIN:            CLR     IC1TRIG
FCFE 12 41 FF 04                     BRSET   IRQTRIG $FF GOBACK
FD02 7E FB 2F                        JMP     RUNMODE
FD05 01                              NOP
FD06 7F 00 41      GOBACK:           CLR     IRQTRIG
FD09 7E F9 CF                        JMP     TOLSET
FD0C CE 10 00      IRQHND:           LDX     #REGBAS
FD0F 86 C8                           LDAA    #%11001000
```

```
FD11 9A 01                      ORAA    LEDOUT
FD13 A7 04                      STAA    PORTB,X
FD15 84 F7                      ANDA    #%11110111
FD17 A7 04                      STAA    PORTB,X
FD19 86 FF                      LDAA    #$FF
FD1B 97 41                      STAA    IRQTRIG
FD1D 01                         NOP
FD1E 01                         NOP
FD1F 01                         NOP
FD20 3B                         RTI
FD21 CE 10 00           COPOUT: LDX     #REGBAS
FD24 86 80                      LDAA    #%10000000
FD26 A7 04                      STAA    PORTB,X
FD28 20 F7                      BRA     COPOUT
FD2A 86 C0              CPMHND: LDAA    #%11000000
FD2C A7 04                      STAA    PORTB,X
FD2E 18 FE FF FF                LDY     $FFFF
FD32 18 3C              NEXT1:  PSHY
FD34 18 FE FF FF                LDY     $FFFF
FD38 18 3C              NXT:    PSHY
FD3A 18 FE FF FF                LDY     $FFFF
FD3E 18 09              NXT4:   DEY
FD40 36                         PSHA
FD41 37                         PSHB
FD42 3D                         MUL
FD43 33                         PULB
FD44 32                         PULA
FD45 2F 02                      BLE     LVL4
FD47 20 F5                      BRA     NXT4
FD49 18 38              LVL4:   PULY
FD4B 18 09                      DEY
FD4D 2F 02                      BLE     LVL1
FD4F 20 E7                      BRA     NXT
FD51 18 38              LVL1:   PULY
FD53 18 09                      DEY
FD55 2F 02                      BLE     END1
FD57 20 D9                      BRA     NEXT1
FD59 86 80              END1:   LDAA    #%10000000
FD5B A7 04                      STAA    PORTB,X
FD5D 18 FE FF FF                LDY     $FFFF
FD61 18 3C              NEXT2:  PSHY
FD63 18 FE FF FF                LDY     $FFFF
FD67 18 3C              NXT2:   PSHY
FD69 18 FE FF FF                LDY     $FFFF
FD6D 18 09              NXT3:   DEY
FD6F 36                         PSHA
FD70 37                         PSHB
FD71 3D                         MUL
FD72 33                         PULB
FD73 32                         PULA
FD74 2F 02                      BLE     LVL3
FD76 20 F5                      BRA     NXT3
FD78 18 38              LVL3:   PULY
FD7A 18 09                      DEY
FD7C 2F 02                      BLE     LVL2
FD7E 20 E7                      BRA     NXT2
FD80 18 38              LVL2:   PULY
```

```
FD82 18 09                    DEY
FD84 2F A4                    BLE    CPMHND
FD86 20 09                    BRA    NEXT2
FD88 20 FE       ILLHND:      BRA    ILLHND
FD8A 01                       NOP
FD8B 20 FE       IC2HND:      BRA    IC2HND
FD8D 01                       NOP
FD8E 20 FE       IC1HND:      BRA    IC1HND
FD90 01                       NOP
FD91 20 FE       XIQHND:      BRA    XIQHND
FD93 01                       NOP
FD94 20 FE       SWIHND:      BRA    SWIHND
FD96 01                       NOP
Errors: 0
```

We claim:

1. A photoelectric color sensor comprising:

at least two light sources disposed in a fixed array focused upon a sensing region, each said source operable to emit light having a limited characteristic range of chromaticity differing from the characteristic range of chromaticity of each other light source;

photosensitive means positionally fixed with respect to said array and region to receive light from each said light source reflected off of a target object within said sensing region and to output a signal in response thereto; and logic means in circuit with said light sources and photosensitive means operative to sequentially energize said light sources and to receive resultant sample signals from said photosensitive means in response to each said light source energization, said logic means being further operative to generate a resultant signal as a function of said sample signals, to compare said resultant signal with a predetermined reference standard and generate a condition output signal when the difference between said resultant signal and reference standard exceeds a tolerance limit, wherein said reference standard has been established during an earlier test mode operation of said logic means in which a standard color mode operation of said logic means in which sensing region and sequentially illuminated by said light sources, said reference standard and said resultant signal comprising a respective single signal for each said characteristic range of chromaticity.

2. A photoelectric color sensor comprising:

a plurality of solid state light sources each said light source operable to emit light having a limited characteristic range of chromaticity substantially differing from the characteristic range of chromaticity of each other light source;

at least one solid state photosensitive element operable to receive light within collective ranges of chromaticity of said state light sources and output an electrical signal in response thereto;

means operative to position said solid state light sources and photosensitive element in a fixed array whereby said sources are commonly focused on a sensing region to reflect light off of a colored target object within said sensing region to said photosensitive element; and logic means in circuit with said light sources and photosensitive element operative to sequentially energize said light sources and to receive resultant sample signals from said photosensitive element in response to each said light source energization, said logic means being further operative to generate a resultant signal as a function of said sample signals, to compare said resultant signal with a predetermined reference standard and to generate a condition output signal when the difference between said resultant signal and reference standard exceeds a tolerance limit, wherein said reference standard has been established during an earlier test mode operation of said logic means in which s standard color object was momentarily disposed in said sensing region and sequentially illuminated by said light sources, said reference standard and said resultant signal comprising a respective single signal for each said characteristic range of chromaticity.

3. The color sensor of claim 2, wherein said plurality of solid state light sources comprise three light emitting diodes operative to emit light in the red, blue and green frequency spectrum, respectively.

4. The color sensor of claim 3, wherein said light emitting diodes are accurately spaced upon a common plane with said sensing region.

5. The color sensor of claim 4, wherein said blue light emitting diode is centrally spaced with respect to said red and green light emitting diodes.

6. A photoelectric color sensor comprising:

a plurality of solid state sources of light, each said source operable to emit light having a characteristic limited range of chromaticity substantially differing from the characteristic range of chromaticity of each other light source;

at least one solid state photosensitive element operable to receive light within the collective range of chromaticity of said solid state sources and output an electrical signal in response thereto;

means operative to position said solid state sources and photosensitive element in a fixed array whereby said sources are commonly focused on a sensing region to reflect light off of a colored target object within said sensing region to said photosensitive element; and logic means in circuit with said light sources and photosensitive element operative to sequentially energize said light sources and to receive resultant sample signals from said photosensitive element in response to said light source energization, said logic means being further operative to generate a resultant signals as a function of said sample signals, to compare said resultant signal with a predetermined reference standard and to generate a condition output signal when the difference between said resultant signal and reference standard exceeds a tolerance limit, wherein said plurality of solid state light sources comprise three light emitting diodes operative to emit light in the red, blue and green frequency spectrum, respectively, said light emitting diodes are accurately spaced upon a common plane with said sensing region, and said at least one photosensitive element comprises first and second phototransistors straddling the central light emitting diode and accurately spaced therewith upon a second common plane with said sensing region.

7. A photoelectric color sensor comprising:
three light emitting diodes operative to emit light in the red, blue and green frequency spectrum, respectively;
two phototransistors operable to receive red, blue and green light from said diodes and output an electrical signal in response thereto;
means operative to position said diodes and phototransistors in a fixed array whereby said diodes are accurately spaced upon a common plane and focused on a sensing region to reflect light off a colored target object within said sensing region to said phototransistors, and said phototransistors are accurately spaced straddling the central diode upon a second common plane with said sensing region; and
logic means in circuit with said diodes and phototransistors operative to sequentially energize said diodes and to receive resultant sample signal from said phototransistors in response to said diode energization, said logic means being further operative to generate a resultant signal as a function of said sample signals, to compare said resultant signal with a predetermined reference standard and to generate a condition output signal when the difference between said resultant signal and reference standard exceeds a tolerance limit.

8. The color sensor of claim 6, wherein said common plane and second common plane are normal.

9. The color sensor of claim 8, said light emitting diodes and phototransistors are equidistant from said sensing region.

10. The color sensor of claim 6, wherein said logic means comprises first amplifier means operative to generate a first element signal in response to said light source energization, second amplifier means operative to generate a second element signal in response to said light source energization and third amplifier means operative to output said sample signals as a function of both said first and second element signals.

11. The color sensor of claim 10, wherein said third amplifier means is operative to output said sample signals as a function of the sum of said first and second element signals.

12. The color sensor of claim 10, wherein each of said phototransistors comprise a characteristic base junction and said logic means comprises means operative to drain electrical current from the base junctions of said phototransistors whenever all of said light emitting diodes are deenergized to offset the effect of ambient induced photocurrent in said phototransistors.

13. The color sensor of claim 2, wherein said light source chromaticity ranges collectively substantially encompass the entire visible light frequency spectrum.

14. The color sensor of claim 2, wherein said logic means comprises a tolerance set circuit operable to establish said tolerance limit.

15. The color sensor of claim 2, wherein said logic means comprises a memory element.

16. The color sensor of claim 15, wherein said predetermined reference standard comprises digitized reference values corresponding with one or more predetermined standard colors stored in said memory element.

17. The color sensor of claim 15, wherein said logic means is operative to generate said resultant signal as a function of predetermined conversion functions stored in said memory element.

18. The color sensor of claim 15, wherein said logic means is further operative to receive and store a plurality of said sample signals in said memory element, to sum said sample signals and to generate said resultant signal as a function of the average value of said stored sample signals.

* * * * *